(12) United States Patent
Munekane et al.

(10) Patent No.: US 7,736,893 B2
(45) Date of Patent: Jun. 15, 2010

(54) NANOBIO DEVICE OF IMITATIVE ANATOMY STRUCTURE

(75) Inventors: Masanao Munekane, Chiba (JP); Hiroyuki Wada, Chiba (JP); Kouji Iwasaki, Chiba (JP); Toshiaki Fujii, Chiba (JP); Takahiro Ochiya, c/o National Cancer Center Research Institute, 5-1-1 Tsukiji, Chou-ku, Tokyo (JP); Yusuke Yamamoto, Chiba (JP); Takumi Teratani, Yokohama (JP)

(73) Assignees: SII Nanotechnology Inc. (JP); Takahiro Ochiya (JP)

( * ) Notice: Subject to any disclaimer, the term of this patent is extended or adjusted under 35 U.S.C. 154(b) by 0 days.

(21) Appl. No.: 11/353,603

(22) Filed: Feb. 14, 2006

(65) Prior Publication Data

US 2006/0188946 A1  Aug. 24, 2006

(30) Foreign Application Priority Data

Feb. 18, 2005 (JP) .............................. 2005-042995

(51) Int. Cl.
*C12N 5/00* (2006.01)

(52) U.S. Cl. ........................... 435/325; 436/63; 436/43; 435/7.2

(58) Field of Classification Search ................. 250/251; 435/325

See application file for complete search history.

(56) References Cited

U.S. PATENT DOCUMENTS

| 5,608,519 | A  | * | 3/1997 | Gourley et al. | ............... | 356/318 |
| 6,744,038 | B2 | * | 6/2004 | Wang et al. | ................... | 250/251 |
| 6,784,420 | B2 | * | 8/2004 | Wang et al. | ................... | 250/251 |
| 2002/0005354 | A1 | * | 1/2002 | Spence et al. | ............... | 204/450 |
| 2002/0006648 | A1 | * | 1/2002 | Goodman et al. | ........ | 435/173.1 |

FOREIGN PATENT DOCUMENTS

| JP | 2001 356971 | 5/2003 |
| JP | 2002 031980 | 8/2003 |
| JP | 2003 067693 | 11/2003 |
| JP | 2002 192399 | 2/2004 |
| JP | 2002 225933 | 3/2004 |
| JP | 2004 321065 | 11/2004 |
| JP | 2003 143099 | 12/2004 |

OTHER PUBLICATIONS

Kan et al, Cell-culture Palte with Sub-micron Aperture Array for near-field Fluorescent Measurement, IEEE, 2004, p. 399-402.*
Kometani et al, Nozzle-nanostructure fabrication on Glass Capillary by Focused Ion Beam chemical vapro deposition and etching, Japan Journal of Applied Physics, 2003, vol. 42, p. 4107-4110.*
Desai, Micro and nanoscale structures for tissue engineering constructs, Medical Engineering & Physics, 2000, vol. 22, p. 595-606.*
Loos et al, The Use of the focused ion beam technique to prepare cross-sectional transmission electron microscopy specimen of polymer solar cells deposited on glass, Polyner, 2002, vol. 43, p. 7493-7496.*
Khademhosseini et al, Microscale techniques for tissue engineering and biology, PNAS, 2006, vo.13, p. 2480-2487.*
M. Ozkan et al., "Electro-Optical Platform for the Manipulation of Live Cells," Langmuir 2003, vol. 19, No. 5, pp. 1532-1538, American Cancer Society.
Regenerative Medicine, 2005, vol. 14, p. 234, Feb. 10, 2005, Japanese Society for Regenerative Medicine.

* cited by examiner

*Primary Examiner*—Jon P Weber
*Assistant Examiner*—Tiffany M Gough
(74) *Attorney, Agent, or Firm*—Adams & Wilks

(57) ABSTRACT

Objects to be achieved by the invention are to provide a nanobio device in which cultured cells are organized at a high-level in a state near in vivo, and to provide a method of using the nanobio device of imitative anatomy structure. The nanobio device of imitative anatomy structure of the invention is obtained by manufacturing a substrate with a biocompatible substance and arranging a plurality of types of cells thereon in a desired array. A method of manufacturing a nanobio device in the invention includes a step of manufacturing a substrate for a nanobio device by a micromachine processing technique and a step of arranging a plurality of cultured cells on the substrate in a desired array with laser optical tweezers.

13 Claims, 9 Drawing Sheets

TRIAL PRODUCT OF BIODEVICE MANUFACTURED BY DEPOSITION

TRIAL PRODUCT OF BIODEVICE MANUFACTURED BY ETCHING

MOLD FOR SUBSTRATE ETCHED BY FIB

MANUFACTURED SUBSTRATE

ARRAY OF HEK293 CELLS ON NANODEVICE

SCALE BAR : 20μm

ARRAY OF TWO TYPES OF CELLS BY FLAGGED BY Q DOT

A. NORMAL CULTURED STATE    B. CELLS ARRANGED ON THE SUBSTRATE

PHASE DIFFERENCE

FLUORESCENT

SCALE BAR : 30 μm

NANOBIO DEVICE OF IMITATIVE ANATOMY STRUCTURE

BACKGROUND OF THE INVENTION

1. Field of the Invention

The present invention relates to a fusion of a technique in a biotechnology and a nanotechnology that realizes a highly integrated substrate device and, more specifically, to a technique for manufacturing a nanobio device in which a group of cells are arranged in array according to a rule which is formed by imitating a certain anatomy structure.

2. Description of the Related Art

In the field of biotechnology in recent years, individual cell can be controlled freely owing to improvement of laser trapping technique and the like, and a shape having dimensions or design according to an intended use can be processed on a substrate since high-integration degree or high-speed degree of the substrate device is enhanced due to recent development of nanotechnology. This technique has reached a level which intends to manufacturing of a nanobio device in which a group of cells are arranged in array according to a rule obtained by imitating a certain anatomy structure. In other words, organization of a cultured cell on a nanodevice in a high level which is substantially in vivo state, which has been believed to be difficult in the related art is in the course of realization owing to the fusion of these technologies. Consequently, it can be expected as an effective tool only in manufacture of material for regeneration medicine, but also in analysis of intercellular action which has been difficult to be figured out in vitro. On the other hand, exhaustive analysis such as transcriptome analysis using a DNA micro-array method or proteome using two-dimensional electrophoresis and a mass spectrograph is utilized in various fields of medical science and biology, and a high throughput analysis attracts attention. It is because not only understanding of the molecules in individual level, but also exhaustive understanding of diversification of molecular mechanism in a network of cells by the high-throughput analysis is required as the entire gene array retained by each living organism is made known by a genome project or a DNA project. Such tendency of new technology is in the course of developing an age of analysis not only by gene expression or an interaction of proteins, but also on a level of living cells by using a system of nanobio device combined with the high-throughput approach, and establishment of anew system as a successor of a biological test and application to a medicament screening and so on are now in the level of being promised.

Regeneration medicine is one of the fields of research which gets the highest attention recently. The prime reason is that it is expected as a medical practice in a new century which supplements serious lack of transplant internal organs. However, it is still in the level of cell transplant treatment at the present moment, and is not in the level of regenerating the internal organ itself. The reasons why regeneration of the internal organs is not realized are as follows. The internal organ has a regular, but very complicated structure such that the internal organ is composed of a plurality of cells, and that a vascular network for supplying nutrition and oxygen is present therein. Therefore, it has been considered that even though it is possible to provide individual cells, it is very difficult to build an internal organ itself therefrom. In other words, with the conventional technology, it is extremely difficult to arrange and constitute an organization of each internal organ by controlling the cells.

However, owing to innovation of laser manipulator technique and development of micro-fabrication technique in the field of nanotechnology in recent years, the cell itself is now able to enjoy benefits of nanotechnology sufficiently. Accordingly, although it is still far from the level at which the internal organ itself can be regenerated at the present moment, it is now possible to arrange cells as desired in a state of segments of an internal organ on an artificial substrate. Therefore, if the substrate having cells arranged thereon can be built using this technique, a three-dimensional internal organ structure can be manufactured by laminating the same into a plurality of layers. Furthermore, if the substrate can be built with a bio-compatible substance such as collagen or hyaluronic acid, an adverse reaction with respect to the cells can further be reduced, and hence manufacture of an internal organ unit that can be transplanted will also be possible in future in combination with a technique of revascularization.

As a source to be used actually for building an internal organ, a systematic stem cell such as a bone marrow cell or an embryonic-stem cell (ES cell) is considered as one of examples. Although the systematic stem cell has a problem such as cell fusion, there is an advantage such that immunological rejection may not occur in theory since it can be taken from an adult and since it is a cell of his/her own, which is one of factors fascinating for building an internal organ. On the other hand, in a problem regarding the embryonic-stem cell, a way to practical use in the field of medical practice is now being explored since a gene relating to formation of a teratoid tumor, which has been an obstacle for transplantation, is now identified and, as regards immunological rejection, a clone embryo technique for transplanting a somatic nucleus of a patient to a fertilized egg and establishing the embryonic-stem cell is enabled. Further development of research on such stem cells to enable foundation of a system in which these stem cells can be supplied as a source (individual cells) for building an internal organ is required for the internal organ regeneration by means of nanotechnology.

[Non Patent Document 1] Oode K, Furuya T, Harada K, Kawaguchi S, Yamamoto K, Hirano T. Sasaki K. "The development of a cell array and its combination with laser-scanning cytometry allows a high-throughput analysis of nuclear DNA content" Am J Pathol. 157(3) pp. 723-728 September 2000.

[Non Patent Document 2] Teratani Ko, Ochiai Takahiro, "Stem Cell, ES cell—Mesenchymal Stem Cell" Regeneration medicine Vol. 3, No. 4 pp. 126-133, 2004)

SUMMARY OF THE INVENTION

In the circumstances such that the reason why regeneration of the internal organ is not realized is that, as described above, the internal organ is composed of a plurality of cells, and that the internal organ is functioning with a formation of a regular, but complicated structure such as the presence of the vascular network for supplying nutrition and oxygen for living therein, and hence it is difficult to arrange into array and build the internal organ itself even though the individual cells can be prepared, an object to be solved by the invention is to provide a nanobio device for organizing a cultured cell in a high-level which is substantially in vivo state, and to present a method of using the nanobio device of imitative anatomy structure.

A nanobio device of imitative anatomy structure according to the invention is obtained by manufacturing a substrate with a bio-compatible substance and arranging a plurality of types of cells into a desired array thereon.

A method of manufacturing a nanobio device according to the invention includes a step of manufacturing a substrate for the nanobio device by a micro machine processing technique, and a step of arranging a plurality of types of cultured cells in a desired array on the substrate using a laser manipulator.

Another method of manufacturing a nanobio device in the invention includes a step of manufacturing a mold for a substrate for a nanobio device with a micro machine processing technique, a step of manufacturing a substrate formed of a bio-compatible substance using the mold as a plate by a printing technique, and a step of arranging a plurality of types of cultured cells into a desired array on the substrate using a laser manipulator.

When the micro machine technique employs a focused ion beam, a structure is manufactured by cutting by ion etching, deposition, or the like. When it employs a femtosecond laser, a three-dimensional structure is established by punching a hole by irradiating the same, or by focus scanning such as two photon absorption using UV cured resin. The print using the mold as a plate is presented as a method in which a bio-compatible substance such as collagen or hyaluronic acid is applied or a method of manufacturing an imprint by pressing the bio-compatible substance. A method of using the nanobio device of imitative anatomy structure of the invention is presented as a method of using the same as a specimen for a medicament toxicity test or a material for a regenerated tissue.

Since the nanobio device of imitative anatomy structure according to the invention is a device in which a highly organized cell array in a living body is regenerated on the substrate of bio-compatible substance such as collagen or hyaluronic acid, a specimen for various tests of the in vivo state in vitro can be provided.

Since a method of manufacturing a nanobio device according to the invention enables acquisition of individual cells and arrangement thereof in a desired array on the substrate of the bio-compatible substance using the technique cultivated in the fields of semiconductor or micro machine and a technique of laser trapping with laser optical tweezers or the like, a highly organized cell array in the living body can be regenerated.

A method of using the nanobio device of imitative anatomy structure according to the invention proposes a usage as the specimen for medicament toxicity test or the material for the regenerative tissue. Therefore, the toxicity test of the medicament can be conducted in a method other than an experiment on a human body or even without using animal, and a result close to in vivo state can be obtained. It can also be used effectively for figuring out of a molecular mechanism in intercellular action. Furthermore, by culturing cells with the nanobio device, a functioning internal organ can be built, and hence development of a technology of building internal organs in the field of regeneration medicine in future is enabled.

DESCRIPTION OF THE PREFERRED EMBODIMENTS

Figure 1:
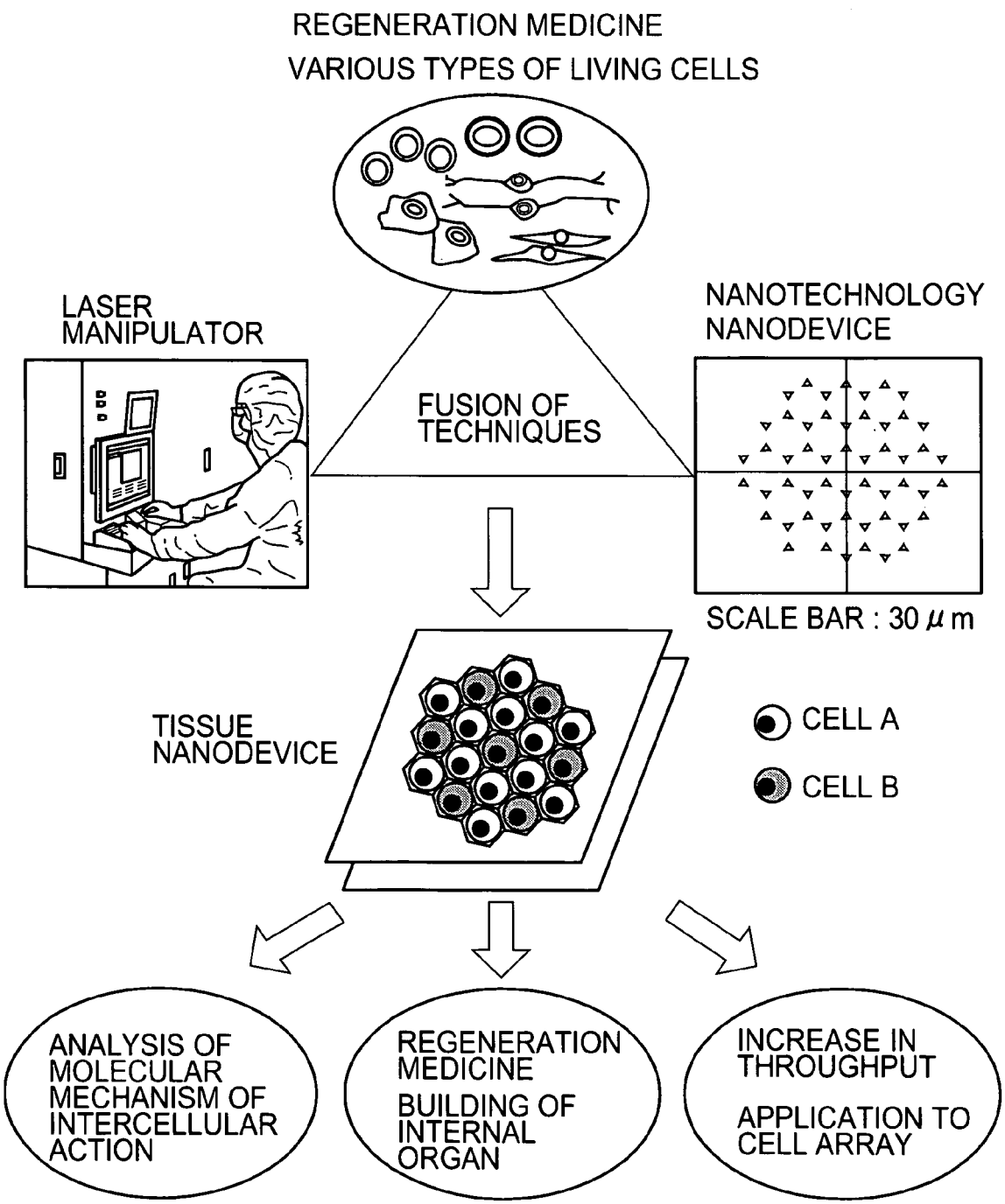
FIG. 1 is a conceptual drawing of the invention.

Referring now to a conceptual drawing in FIG. 1, manufacturing of a nanobio device of imitative anatomy structure according to the invention and an example of application will be described. Various types of living cells which are taken from animals or human bodies are cultured in a conventional method. A substrate for the nanobio device is manufactured using nanotechnology. Cells cultured in advance are acquired using a laser manipulator on the substrate, and arranged the same on predetermined positions to form a tissue nanodevice. In this case, according to the invention, a plurality of types of Cells can be arranged in array in a form imitating the anatomy structure, and the nanobio device of imitative anatomy structure as described above opens up a way to analysis of intercellular molecular mechanism or as a base material for the internal organ building technology in the field of regeneration medicine, or to an application to a high-throughput cell array.

The nanobio device of imitative anatomy structure according to the invention is obtained by building an organ by arranging the cells regularly and into a complex structure and, then in order to maintain the same, it is necessary to supply oxygen or nutrition under an environment suitable for existence of cells. At present, culturing of an internal organ unit is not achieved yet, and hence a substrate (minute structure) suitable for arranging cells intended for culture is necessary. As a base of the invention, the inventors came up with an idea to apply a processing technique using a focused ion beam (FIB) apparatus developed in a semiconductor processing technique in order to manufacture the substrate.

A wiring width for processing, which is a reference mark of performance of a semiconductor, almost reaches a level of fine machining of several tens nanometers in an exposure technique using a short wavelength light source such as an electron beam or an extreme ultraviolet light owing to recent development of a semiconductor technology. In the field of the semiconductor, a "mask" which is a transfer pattern is required for exposure, and the focused ion beam apparatus is employed for processing and correction thereof. The FIB serves as a mask correction tool or as a failure analysis tool for cutting various devices and observing a cross-section thereof using its processing function. Therefore, we focused on the FIB apparatus, and propose manufacturing of a device substrate for culturing cells using the same as a device manufacturing tool in the biological field.

The focused ion beam apparatus will be described briefly before describing a technique to manufacture the substrate. The FIB is an apparatus that electrically derives gallium ion from an ion source, converges the same by an electrostatic lens and irradiates the same onto an object as a beam. Shape observation like a Scanning Electronic Microscope (SEM) is enabled by scanning a minute area on the object with the beam which is converged into a thin shape. This function is referred to as Scanning Ion Microscope (SIM). The difference between the SIM and the SEM is that the SEM is mainly used for observation while the SIM is used also for processing in addition to observation and is capable of irradiating the ion beam at a desired position and cutting the same by sputter etching.

Furthermore, the FIB scans the surface of the minute area on the object with a beam while spraying specific gas such as phenanthrene $C_4H_{10}$ thereon so that components in the compound gas are anchored on the irradiated area. Therefore, the FIB can cause the components in the compound gas to be anchored and accumulated locally at desired position on the surface of the specimen. This accumulation of a film is referred to as Ion Induction Chemical-Vapor-Deposition (CVD). With deposition, various types of films can be accumulated by changing the type of gas. When deposition is performed by spraying phenanthrene, an amorphous film called diamond-like carbon is accumulated. The FIB has a function to form a desired shape on the surface of the specimen by combining the functions of observation, the etching, and the deposition.

A merit to apply the FIB processing technique for manufacturing the device is that the FIB is superior in that desired fine shaped processing can quickly be performed by the cutting function by etching described above and the building function by deposition, and in particular, in that it satisfies favorable terms by having a capability to build the minute structure in a bottom-up processing, so that a desired structure can be provided by keeping pace with needs in the field of biotechnology.

Figure 2:
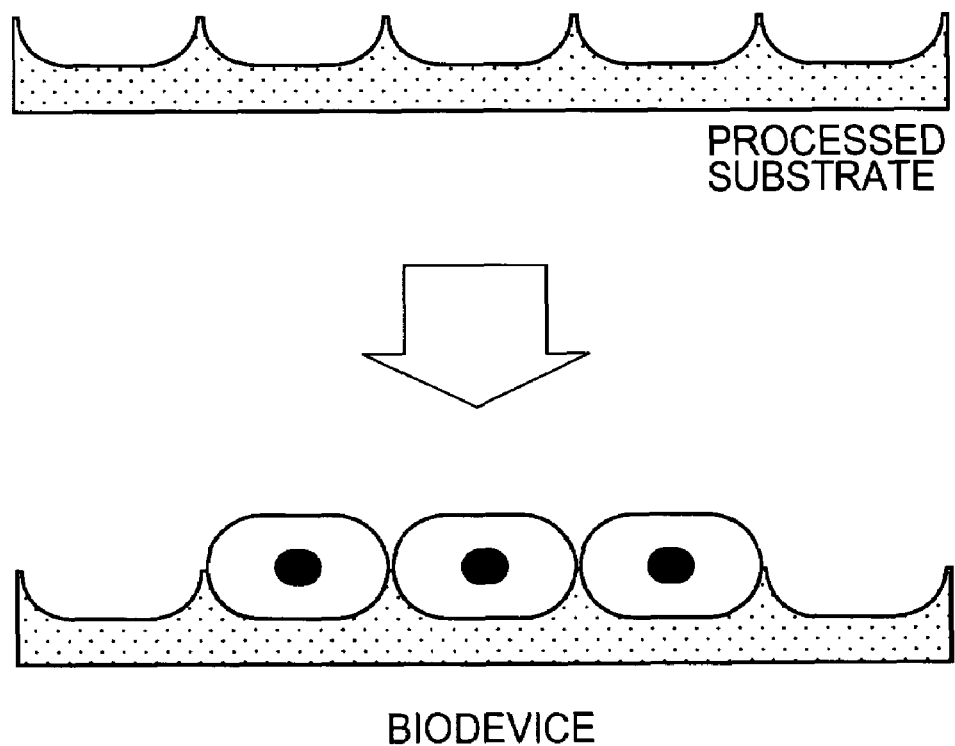
FIG. 2 is a conceptual drawing showing a substrate etching processed with an FIB and having cells placed thereon.

The nanobio device is a substrate intended for arrangement of cells and imaging. The cells are soft and hence they are flattened toward the substrate due to the effect of a gravitational force. Therefore, it is configured to have dimensions considering the change of the shape, and arranged not to cause the adjacent cells to be completely partitioned from each other, but to come into contact with each other for achieving interaction. The shape is required to be such that the cells can be activated as a device for imaging the interior of the living body as much as possible. FIG. 2 schematically shows a mode described above.

Figure 3:
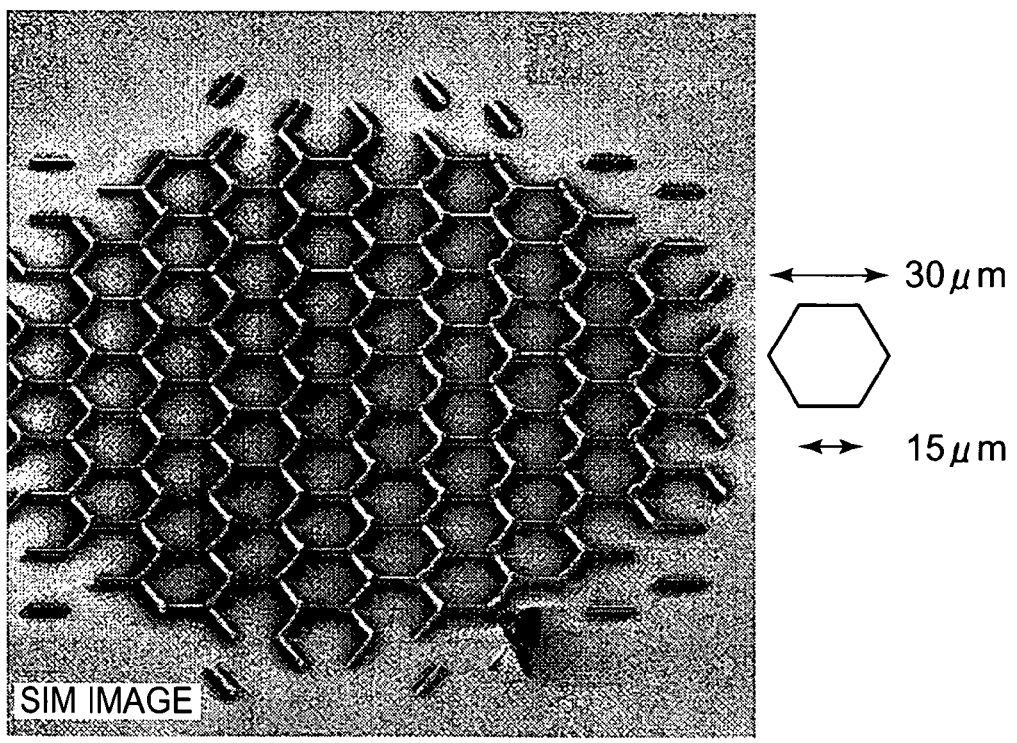
FIG. 3 is an image of a substrate processed by deposition viewed through an ion microscope.

A form of a trial product of the nanobio device manufactured by the deposition function of the FIB will be shown in FIG. 3. The processing time required was about 2 hours including observation. A wall structure shown in an SIM image in FIG. 3 was manufactured on a silicon substrate, which was used for a semiconductor wafer in a deposition process. The walls were formed as partitions for arranging hepatic cells, so that the cells come in contact with each other at portions higher than the walls or partitions when the cells were arranged in each of the chambers. From the result of the experiment, it was found that a specimen base for stably arranging the hepatic cells could be manufactured in a short time.

Figure 4:
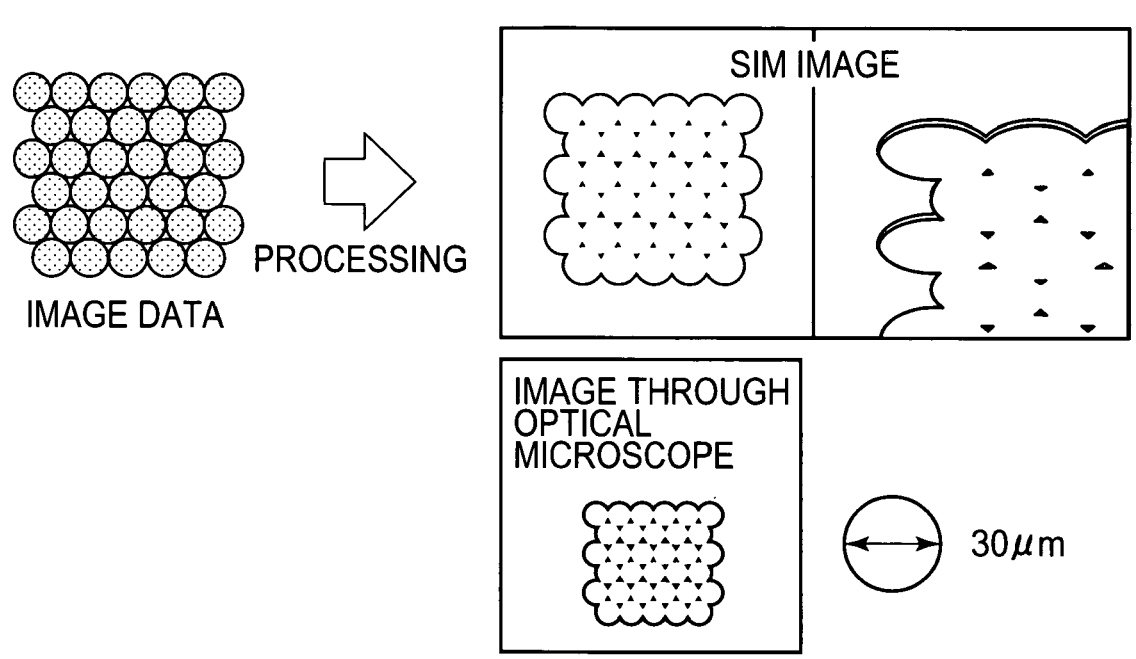
FIG. 4 is a drawing showing a substrate manufactured on the basis of an image data as a trial product.

Subsequently, a form of a trial product of the nanobio device manufactured by the etching function of the FIB will be shown in FIG. 4. Since visible light is used for imaging observation of living cells colored by fluorescent coating, a transparent substrate is suitable. However, the diamond-like carbon or the silicone substrate manufactured by the deposition shown in FIG. 4 does not allow passage of light. Therefore, an ITO substrate, which was a transparent conductive substrate, (a glass substrate formed with indium oxide) was selected for allowing easy observation by an optical microscope, and etching form processing was applied on the substrate. The form processing was performed using specific software on the basis of an image data for processing, and the form of an obtained structure was confirmed by oblique SIM image observation, and light permeability was confirmed via the observation with the optical microscope. The ITO substrate can prevent a charging phenomenon (charge-up) caused by irradiation of a charged beam of the SIM or the SEM in comparison with the glass substrate, and deterioration of processing accuracy can advantageously be constrained.

Figure 5:
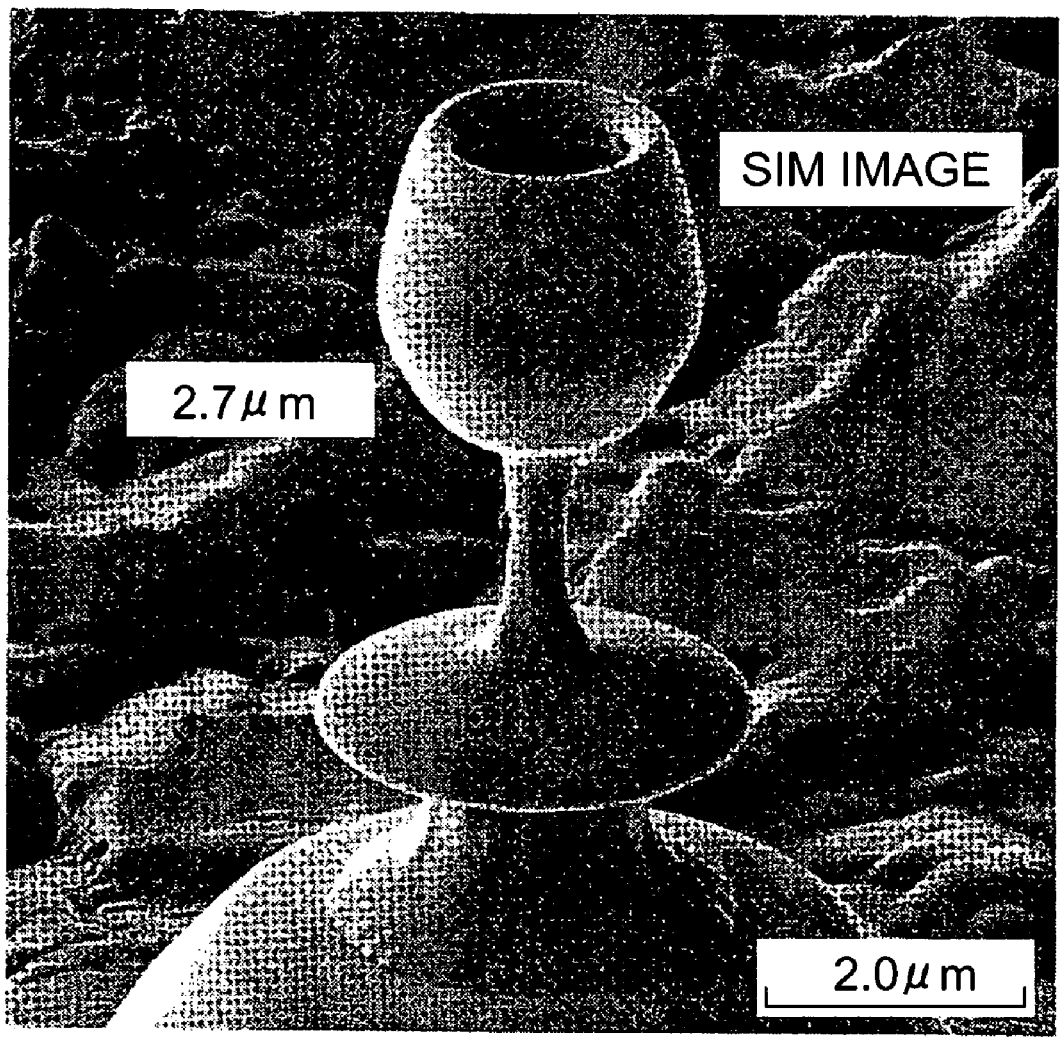
FIG. 5 is an example of a trial product of a wine glass showing a precision level of an FIB processing.

In order to show a manufacturing capability of the FIB, a rotary glass, which is a structure manufactured by the combination of etching and deposition is shown. The rotary glass shown in FIG. 5 was manufactured by manufacturing a base material with the diamond-like carbon in advance according to the deposition process on a high-accuracy rotary stage, whose axial deflection was minimized, and performing etching process by irradiating the FIB from right beside while rotating the same at 200 rpm. A hole on top of the glass was also formed by cutting the same from above with the FIB. The upper portion of the glass was $\phi 2.7$ μm, an opening of the glass was 2 μm $\phi$ or smaller, and hence it is understood that it was a smaller structure in comparison with a cell organ. We refer this function to as "nano turning machine" which is a novel minute structure manufacturing tool using the FIB.

Alternatively, there is a method for manufacturing a three-dimensional structure by taking a three-dimensional data as an image. In this method, an appearance model is manufactured by deposition while reflecting information on the contour of a human chromosome obtained by an atomic force microscope (AFM) or the like. An image data in a plurality of sections from an AFM measuring data (three-dimensional information) in culture solution and the deposition is executed on the basis of the image, so that a three-dimensional structure in the same scale in the X-Y direction is established. In this manner, manufacture of the minute structure on the basis of the image data with the form reflected thereto is possible both by the etching process and the deposition process.

Figure 6A:
FIGS. 6A-6C are schematic drawings of a mold for the substrate etching processed with the FIB, and imprinting operation using the mold as a plate.
Figure 6B:
Figure 6C:
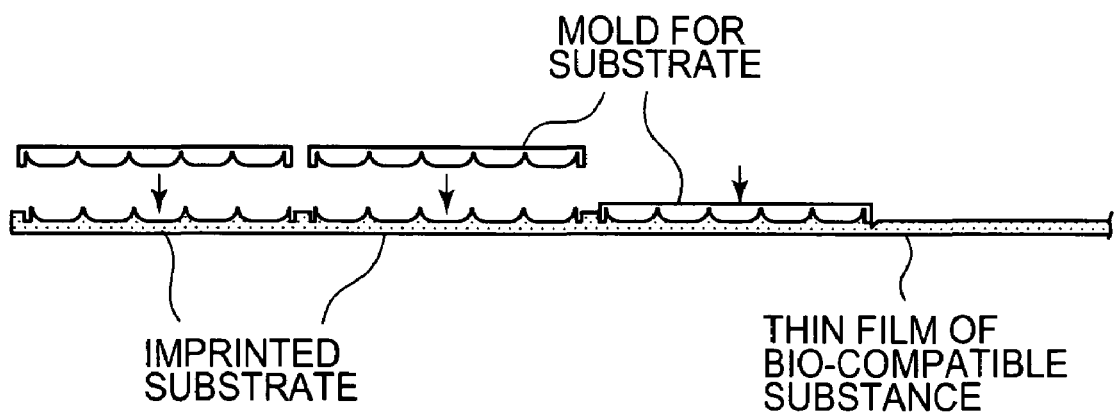

A substrate is manufactured by an imprint technique this time using a plate formed by the FIB processing technique. Mass production in future will be enabled by this imprint technique. The imprint technique is intended to form a rough-surface plate by applying the fine processing to a desired material as a mold and manufacture a plurality of products repeatedly. The nano-imprint technique is expected as a processing technique for future generation which enables processing on the order of ten nanometer level also in the field of the semiconductor. According to an imprinting method in the invention, as schematically shown in FIGS. 6A-6B, a mold for a nanobio device is manufactured first with the FIB. The form of the mold shown in FIG. 6A is a form inverted from a form required for the substrate shown in FIG. 6B in terms of projection and depression. As shown in FIG. 6C, the structure shown in FIG. 6B is obtained by transferring the structure shown in FIG. 6A, which is obtained by applying the etching process with the FIB, as a negative plate to a bio-compatible thin film such as collagen. The substrate which was actually transferred was verified with the AFM in terms of the form accuracy, and proved to have a high manufacturing capability. Although the FIB has a superior performance for manufacturing structures in the micrometer level, it requires long time for processing a wide range over a millimeter. Therefore, the nano-imprint technique is more efficient for mass production than by processing the substrate itself with the FIB.

When the manufacture of the substrate is completed, cells are arranged one-by-one thereon. This manipulation is performed by using the laser trapping technique. A function which is required in this manipulation is to acquire the fine cells one-by-one and to transport the same to predetermined positions on the substrate, and hence a laser manipulator system, which is referred to as "laser optical tweezers", is used. A principle of a light trapping using the LMT system is as follows. When a laser is irradiated on a fine substance such as a cell in a converged manner, the laser beam refracts due to the difference in medium, and hence the kinetic momentum of light is changed. A plurality of laser beams are irradiated onto the fine substance, the combined kinetic momentum of light acts on the fine substance, and at this time, a force in the opposite direction is generated for storing the kinetic momentum, and consequently, the fine substance is trapped by a focal point. By moving a specimen stage in this state, the acquired fine substance is relatively moved. If a container for the cultured cells and the specimen substrate are placed on the specimen stage, the manipulation required in the invention can be achieved. This manipulation can be performed while observing with the optical microscope of high power with a provision of a CCD camera set thereon.

Application of the invention for figuring out the intercellular action which is enabled by the nanobio device manufactured according to the invention will be described. Since the arrangement of the cells is possible as desired on the substrate, application of the same for figuring out of the intercellular action is also expected. At the present, a number of experiments that can regenerate the in vivo state in vitro by using a co-cultured system including two or more types of cells or an ex vivo system using brain tissues cultured in slice are reported. The method using a nanodevice for internal organs intended by the invention enables regeneration of cell array organized at a high-level in the living body better in comparison with the co-cultured system, and being different from the slice culturing system, only the cells that the inspector wants to see the function may be selected and arranged. Therefore, a simpler system can be built and hence it is suitable for observing a dynamic state or the function of the cells. Furthermore, since the cells can be arranged as desired, it is also possible now to build a cell array which does not exist in an actual living body for performing an assay. An important merit is that intercellular actions of at least two types of cells, such as a hepatic cell and a vascular endothelial cell or a hepatic cell and a fibroblast can be inspected for each array. However, in comparison with the normal culturing method, it is difficult to arrange a large number of cells in a short time with this method at this moment, and it is now in the stage of being capable of building a small scale of cell group. Therefore, it is necessary to measure gene expression or cell function via bio-imaging for individual cells using a method of extremely high detection sensitivity (such as a reporter gene assay using luciferase).

At the moment, an analysis achieving a high throughput represented by a DNA micro array analysis and so on attracts attention. This analysis enables acquisition of a large number of gene expression profiles at a time by providing as many as several ten thousands of DNA probes on a chip. This technique is reported to be effective for diagnosis of cancer tissue (see Non Patent Document 1) in a field of research of clinical medicine. In other words, in association with enhancement of throughput, the scale of experiment is reduced and a huge amount of data can be obtained. Therefore, by developing a function analyzing system which achieves a high throughput at the cell level by combining the nanodevice for internal organs according to the invention with an approach such as the cell array, it is expected that a tool effective for analyzing the effect of introduction of medicaments or genes is obtained. In other words, many types of cells (established cell line or primarily cultured cell) can be analyzed in vitro at a high throughput in the state closer to in vivo. Accordingly, by analyzing individual cells separately, information on gene expression including information on intercellular action which could be hardly understood taken into consideration will be able to be obtained, which can be used as very effective means in the field of research.

Figure 7:
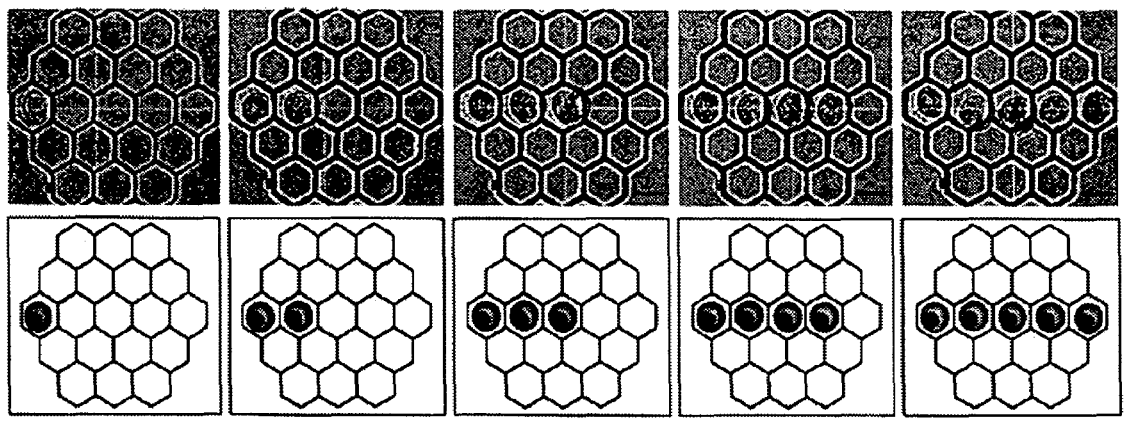
FIG. 7 is a drawing showing a state in which HEK 293 cells are arranged in sequence on the substrate.
Figure 8:
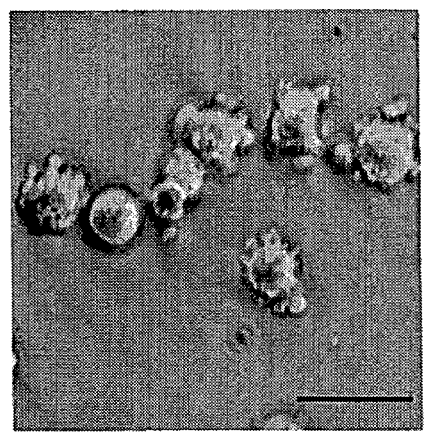
FIG. 8 shows microphotographic images showing that two types of identifiable cells can be arranged on the substrate in a desired array.
Figure 8:
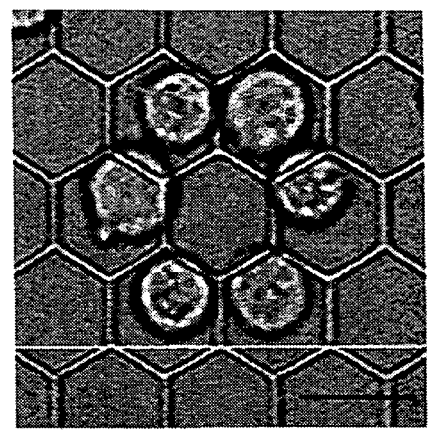
Figure 8:
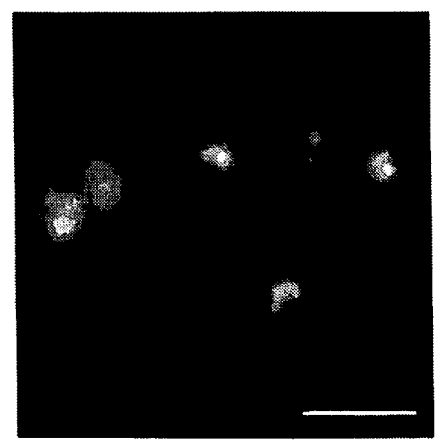
Figure 8:
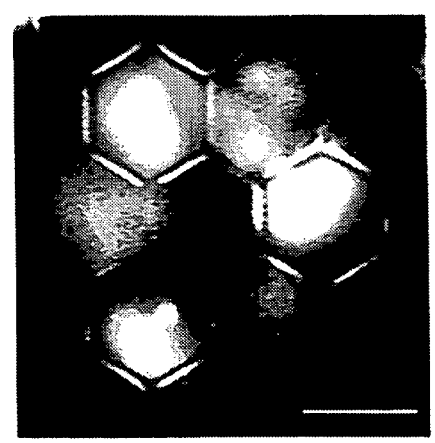

A state in which arrangement of cells actually on the substrate by manipulating the cells on one-by-one basis is enabled by the technique of the invention is shown in FIG. 7. Microphotographic images shown on the upper stage show sequence in which cells are transferred onto the substrate formed with barriers in honeycomb pattern one-by-one using laser optical tweezers, and those shown on the lower stage are schematic drawing showing the same sequence for easy understanding. The length of the scale bar on the lower right of the microphotographic image is 20 µm. They are arranged linearly on one-by-one basis. Subsequently, in order to prove that a plurality of types of cells can be arranged on the nanodevice substrate by manipulating the cells, an experiment of arranging HEK293 cells that are flagged typically by two types of Q dot (quantum dot) reagent (655 red, 565 green; QUANTUM DOT CORPORATION, SC BioSciences Corporation) so as to be capable of being identified on the nanodevice with the laser manipulator (laser optical tweezers) was conducted. Appearances during this experiment are shown in FIG. 8. A state of normal culturing in a Petri dish is shown in A in FIG. 8, and a state of being arranged on the substrate for nanobio device in the invention is shown in B in FIG. 8. When the two types of cells differently dyed by Q dot are cultured as normal in the Petri dish, the cells are arranged at random irregularly as shown in A. A state in which the two types of cells are manipulated by the laser manipulator and are acquired and transferred onto the substrate alternately into a ring-shape is shown in B in FIG. 8. The upper images are phase difference images and the lower images are fluorescent photographs in B. The length of the scale bar is 30 µm. Although they are slightly unclear since they cannot be shown in colors, it will be understood that cells dyed in red and cells dyed in green are arranged regularly in sequence in the fluorescent photographs. The cells could be arranged regularly as in the photographs. This means that various arrays can be generated freely. It will be understood from FIG. 8 that the cells move at random in the normal culture in the Petri dish as will be seen in the upper and lower photographs in A, while the cells are fixed in the chambers on the substrates according to the invention.

Figure 9:
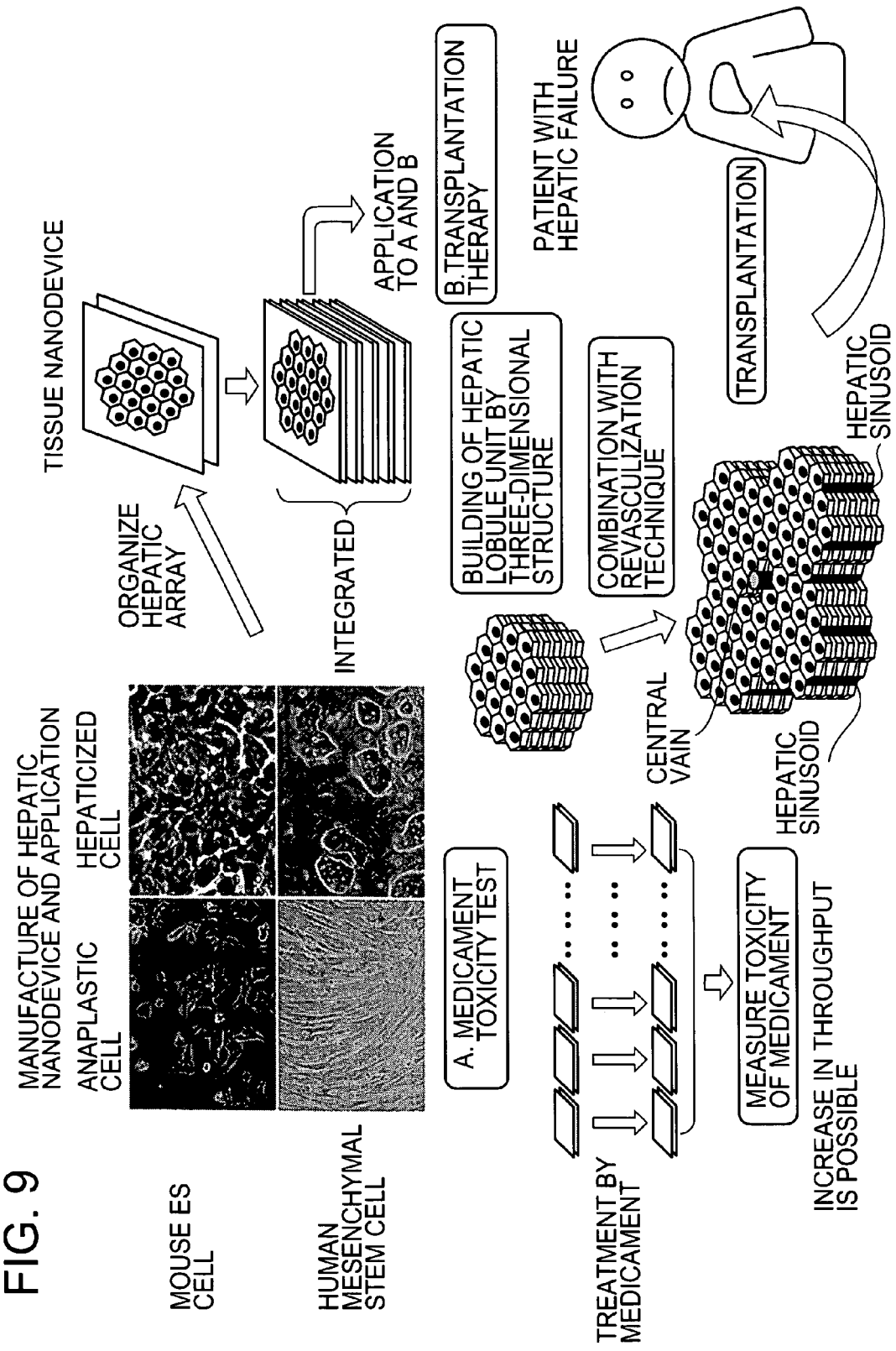
FIG. 9 is an explanatory drawing showing manufacture of a hepatic nanodevice and an application thereof.

Referring now to FIG. 9, a hepatic nanodevice will be shown as an example of application. The inventors regenerated a hepatic lobule structure of a liver on the nanodevice, and are in the course of manufacturing the hepatic nanodevice. The inventors are now setting out to establish a system in which screening of medicaments such as anti-cancer drugs can be performed at a high-throughput using the hepatic nanodevice in a safety test for medicaments. In FIG. 9, microphotographic images of anaplastic cells and hepaticized cells for ES cells of a mouse and the mesenchymal stem cells of a human are shown on the upper left side. The term anaplastic means the cells in a state being sampled, and the term hepaticized means processed into the hepatic cells. The array of the liver tissue is regenerated and organized on the substrate using the hepaticized cells with the technique of the invention. This state is schematically shown as the tissue nanodevice on the upper right side of the drawing.

The fact that the hepatic parenchyma cell being cultured three-dimensionally is improved in hepatic function and kept for a long term in comparison with the case of being cultured in a single layer is reported. It is known that the liver is composed of a plurality of types of cells such as the vascular endothelial cells and epithelial cell of a biliary tract in addition to the hepatic parenchyma cells, and the hepatic function is improved in the co-culturing system including these cells. Therefore, aiming to further improvement of the function of the hepatic parenchyma cells, the inventors came up with an idea to arrange other types of cells in addition to the hepatic parenchyma cells as a main component in the form close to in vivo on the nanodevice substrate. It is because the inventors consider that the function of the hepatic parenchyma cells may further be improved by causing the intercellular action like the in vivo state. In other words, if the function similar to in vivo can be provided to a cell in vitro, the animal experiment using rats or the like can be reduced, which is effective in the viewpoint of cost reduction and ethical concept. The inventors came up with an idea of realizing a method of integrating the hepatic nanodevice into the three-dimensional structure by using a bio material which is high in biodegradability as a material for the nanodevice substrate.

The method of culturing internal organs artificially is shown in the invention. In order to achieve the invention, it is necessary to arrange the hepatic parenchyma cells and other types of cells are arranged on the nanodevice, and to determine an arrangement in which the hepatic function is improved to the maximum. Regarding the cells to be used actually, we, National Cancer Center Research Institute, Section for Studies on Metastasis is successful in differentiation induction from the ES cells or human myeloid stem cell to the hepatic parenchyma cell (see Non Patent Document 2). If the hepatic parenchyma cells obtained from these stem cells can be used for the hepatic nanodevice, the safety test for the medicaments at a high-throughput can be achieved with minimum usage of the animal bodies, and hence the invention will be used as a basic material in the clinical medicine, in particular, in the field of regenerative medical science, or in the wide range of fields including pharmacology and biology.

What is claimed is:

1. A method of producing a nanobio device of imitative anatomy structure, comprising the steps of:
    manufacturing a substrate for a nanobio device by focused ion beam processing, the substrate having an array of chambers with walls formed as partitions that separate the chambers; and
    arranging individual cells, from among a plurality of types of cultured cells, in individual chambers using optical tweezers to permit interaction among the cells to produce a nanobio device of imitative anatomy structure.

2. A method of producing a nanobio device of imitative anatomy structure according to claim 1; wherein the walls are formed so that the cells in adjoining chambers come in contact with each other at portions thereof that are higher than the walls.

3. A method of producing a nanobio device of imitative anatomy structure according to claim 1; wherein the substrate is manufactured by deposition by use of a focused ion beam.

4. A method of producing a nanobio device of imitative anatomy structure according to claim 1; wherein the substrate is manufactured by etching by use of a focused ion beam.

5. A method of producing a nanobio device of imitative anatomy structure according to claim 4; wherein the substrate is manufactured by etching a glass substrate with indium oxide formed thereon, the glass substrate being a transparent conductive substrate.

6. A method comprising the steps of:
    manufacturing a substrate for a nanobio device using focused ion beam processing, the substrate having an array of chambers that are open at the top and that are separated from one another by partitions; and
    arranging individual cells from among plural types of cultured cells in individual chambers using optical tweezers.

7. A method according to claim 6; wherein the manufacturing step includes forming the partitions to a height that permits the cells in adjoining chambers to come in contact with one another over the tops of the partitions.

8. A method according to claim 6; wherein the array of chambers comprises an array of hexagonal chambers.

9. A method according to claim 6; wherein the arranging step includes arranging individual cells of one type in individual ones of some chambers and arranging individual cells of another type, different from the one type, in individual ones of other chambers.

10. A method according to claim 6; wherein the manufacturing step comprises manufacturing the substrate by deposition using a focused ion beam.

11. A method according to claim 6; wherein the manufacturing step comprises manufacturing the substrate by sputter etching using a focused ion beam.

12. A method according to claim 6; wherein the manufacturing step comprises manufacturing a substrate having an array of depressions separated by projections, the depressions constituting the array of chambers and the projections constituting the partitions.

13. A method according to claim 12; wherein the manufacturing step includes dimensioning the depressions and projections to permit cells in adjoining depressions to come in contact with one another over the tops of the projections.

* * * * *